US010448907B2

(12) United States Patent
Inomata

(10) Patent No.: US 10,448,907 B2
(45) Date of Patent: Oct. 22, 2019

(54) X-RAY IMAGING APPARATUS

(71) Applicant: SHIMADZU CORPORATION, Nakagyo-ku, Kyoto-shi, Kyoto (JP)

(72) Inventor: Shuichi Inomata, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 145 days.

(21) Appl. No.: 15/872,542

(22) Filed: Jan. 16, 2018

(65) Prior Publication Data
US 2019/0216414 A1 Jul. 18, 2019

(51) Int. Cl.
A61B 6/00 (2006.01)
A61B 6/08 (2006.01)
G06T 5/50 (2006.01)
H05G 1/60 (2006.01)

(52) U.S. Cl.
CPC .......... A61B 6/4028 (2013.01); A61B 6/08 (2013.01); A61B 6/5241 (2013.01); A61B 6/547 (2013.01); G06T 5/50 (2013.01); G06T 2207/10116 (2013.01); H05G 1/60 (2013.01)

(58) Field of Classification Search
CPC ......... A61B 6/032; A61B 6/54; A61B 6/4028; A61B 6/5241; A61B 6/4233; A61B 6/426; A61B 6/08; G06T 6/547; G06T 2207/10116
See application file for complete search history.

(56) References Cited

U.S. PATENT DOCUMENTS

2010/0290707 A1 11/2010 Wang et al.
2014/0219420 A1* 8/2014 Ishikawa .................. A61B 6/54
378/62

FOREIGN PATENT DOCUMENTS

| JP | 2007-202761 | 8/2007 |
| JP | 2010-233906 | 10/2010 |
| JP | 2012-249789 | 12/2012 |
| JP | 2015-112298 | 6/2015 |

OTHER PUBLICATIONS

JP 2015-136093, 2nd Office Action dated Feb. 28, 2019, 3 pages—Japanese, 3 pages—English.
JP 2015-136093, Notification of Reasons for Refusal dated Aug. 24, 2018, 5 pages—Japanese, 4 pages—English.

* cited by examiner

Primary Examiner — Don K Wong
(74) Attorney, Agent, or Firm — Andrew F. Young, Esq.; Lackenbach Siegel, LLP

(57) ABSTRACT

An X-ray imaging apparatus is capable of cutting the time needed for the long-length image. A candidate point registration element 25 registers an end of a long-length region as a candidate point. A start location determination element 27 determines the candidate point closest to the present location of the imaging system as the imaging start location based on the distance between the present location of the imaging system and each candidate point. A distance that the imaging system shifts at the imaging preparation step of the X-ray images by determining the imaging start location prior to imaging of a series of X-ray images that form a long-length image can be shortened. When the long-length imaging is implemented multiple times, the shift-distance of the imaging system is further shortened by updating the setting of the imaging start location in advance every time when a series of X-ray images is taken, so that the time needed for the entire steps relative to the long-length imaging can be largely cut.

4 Claims, 14 Drawing Sheets

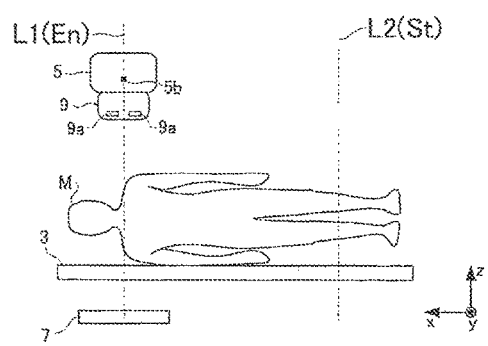 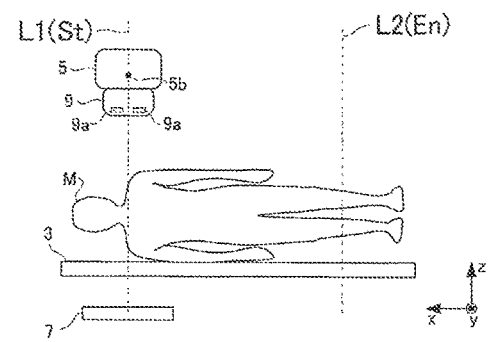
FIG. 5A
FIG. 5B

↓ Fixed setting of St, En

↓ nth imaging start (n + 1)th imaging preparation (n + 1)th imaging start

EMBODIMENT

↓ Setup of St, En is updated by start location determination element

↓

X-RAY IMAGING APPARATUS

CROSS REFERENCE TO RELATED APPLICATIONS

This application relates to, but does not claim priority from, JP 2015-136093 filed Jul. 7, 2017 published as JP 2017-18160 on Jan. 26, 2017, the entire contents of which are incorporated herein by reference.

FIGURE SELECTED FOR PUBLICATION

FIG. 1

BACKGROUND OF THE INVENTION

Field of the Invention

The present invention relates to an X-ray imaging apparatus that acquires an X-ray image of a subject using an X-ray, and particularly, relates to the X-ray imaging apparatus that generates the X-ray image taking the long-length imaging range in the body-axis direction of the subject.

Description of the Related Art

In a medical site, a long-length imaging that takes a single X-ray image (long-length image) that includes the long-length imaging region, e.g., from the neck to the knee of the subject, in the body-axis direction of the subject as the imaging object. In such case, it is difficult to take a long-length image relative to the long-length imaging range by one X-ray radiation due to the specification of the X-ray detector. Therefore, the long-length image is taken by the long-length imaging that implements an X-ray imaging multiple times while shifting the X-ray irradiation field. Relative to a long-length imaging, a plurality of X-ray images is taken along the body-axis direction of the subject and the long-length image is obtained by connecting such plurality of X-ray images in the body-axis direction and reconstructing therefrom (e.g., Patent Document 1, 2).

The inventor sets forth an X-ray imaging apparatus that is applied to a long-length imaging. Referring to FIG. 7A, a conventional X-ray imaging apparatus 100 comprises a tabletop 101 on which a subject M is loaded, an X-ray tube 103 that irradiates an X-ray 103a to the subject M, and an X-ray detector 105 that detects the X-ray and outputs an X-ray detection signal. A collimator 107 that narrows (limits) the X-ray 103a to the predetermined shape is installed to the inferior part of the X-ray tube 103. The X-ray tube 103 and the X-ray detector 105 constitutes an imaging system and each of the imaging system shifts in the x-direction, i.e., the longitudinal direction of the table 101. The imaging system movement mechanism 109 controls the shifting each of the imaging system.

An image generation element 111 is installed in the inferior of the X-ray detector 105 and a reconstruction element 113 is installed in the inferior of the image generation element 111. The image generation element 111 generates a plurality of X-ray images based on the X-ray detection signal output from the X-ray detector 105. The reconstruction element 113 connects each X-ray images, which the image generation element 111 generates, in the body-axis direction of the subject M to reconstruct the long-length image. The main control element 115 controls each of an imaging system shifting mechanism 109, the image generation element 111, and the reconstruction element 113 in accordance with the directive content that an operator inputs through the input element 117.

In addition, the input element 117 specifies the imaging start location and the imaging end location relative to the long-length imaging. The imaging start location is the location of the imaging system when imaging the first X-ray image of the X-ray images that are applied to the reconstruction of the long-length image. The imaging end location is the location of the imaging system when imaging the last X-ray image. Referring to FIG. 7B, the input element 117 comprises a start location registration switch 117a, an end location registration switch 117b, an imaging preparation switch 117c, and an imaging start switch 117d.

Next, referring to the flow-chart of FIG. 8, the inventor sets for the long-length imaging using a conventional X-ray imaging apparatus 100. First, the imaging start location is registered relative to the long-length imaging. Referring to FIG. 9A, the operator shifts each of the imaging system to the appropriate location L1 as the imaging start location while making sure the locational relationship between the subject M and the imaging system. Then, the operator presses down the start location registration switch 117a that is installed to the input element 117 so that the operator can register the present location L1 of the imaging system as the imaging start location (step S1).

Referring to FIG. 9B, the operator shifts each of the imaging system to the appropriate location L2 as the imaging end location while making sure the locational relationship between the subject M and the imaging system following registration of the imaging start location L1. Then, the operator presses down the end location registration switch 117b so that the operator can register the present location L2 of the imaging system as the imaging start location (step S2). The imaging start location L1 and the imaging end location L2 are registered, so that the long-length region W is determined.

Referring to FIG. 10A, after determining the long-length region W, the operator pressed down the imaging preparation switch 117c so that each of the imaging system shifts to the imaging start location L1 and in addition, the collimator 107 adjusts the X-ray irradiation field (step S3). The collimator 107 adjusts the X-ray irradiation region to become a rectangular region having the width T in the x-direction (body-axis direction of the subject M).

Subsequently, once the operator presses down the imaging start switch 117d, the imaging of the X-ray image starts. Specifically, referring to FIG. 10B, each of the imaging system shifts from the imaging start location L1 to the imaging end location L2. And an X-ray 103a irradiation is repeated every time when the X-ray tube 103 shifts the distance corresponding to the width T in the X-direction (step S4). The X-ray detector 105 detects the X-ray 103a and outputs the X-ray detection signal; and the image generation element 113a generates an X-ray image based on the X-ray detection signals. The X-ray image is generated every time when the X-ray 103a is irradiated, so that a plurality of the X-ray images having the width T in the x-direction relative to the range of the long-length region W at the step S4.

Once each X-ray image is taken, the reconstruction element 113 connects a plurality of X-ray images, which the image generation element 111 generates, in the body-axis direction (x-direction) of the subject M to reconstruct the single long-length image (step S5). In such way, the imaging start location L1 and the imaging end location L2 are registered by operating the each of the switches 117a-117d, and the long-length imaging is implemented based on the registered location data of the imaging start location L1 and the imaging end location L2.

RELATED PRIOR ART DOCUMENTS

Patent Document

Patent Document 1
  JP 2007-202761 A1
Patent Document 2
  JP 2012-249789 A1

ASPECTS AND SUMMARY OF THE INVENTION

Objects to be Solved

Nevertheless, in the case of a conventional example having such structure, following problems are remained to be solved.

Specifically, when the long-length imaging is implemented, the long-length imaging relative to the long-length region W may have to be implemented multiple times. For example, it is the case in which after the first long-length imaging is implemented on the supine subject M (referring to FIG. 10A, 10B), the body position of the subject M is changed to the lateral decubitus posture to implement the second long-length imaging (referring to FIG. 10C, 10D). According to the conventional X-ray imaging apparatus, the predetermined location is registered as the imaging start location or the imaging end location.

Accordingly, when the conventional X-ray imaging apparatus implements the long-length imaging multiple times, the imaging system relative to the first long-length implements first takes an X-ray image while shifting from the imaging start location L1 to the imaging end location L2 (referring to FIG. 10A, 10B). Next, referring to FIG. 8, when the second long-length imaging is implemented, the step backs to the step S3 from the step S5 and repeat the steps from the step 3 to the step 5.

Specifically, the imaging system located at the imaging end location L2, at the time when the step S5 relative to the first imaging ends, is shifted to the imaging start location L1 at the step S3 relative to the second imaging (referring to FIG. 10C). Subsequently, each of the imaging system shifts again from the imaging start location L1 to the imaging end location L2 at the step S4 relative to the second imaging (referring to FIG. 10D). Therefore, according to the conventional apparatus, when n times of the long-length imaging are implemented, each of the imaging system must shift back-and-forth at least (2n−1)/2 times between the location L1 and the location L2 (between both ends of the long-length region W). As results, the time needed to complete the long-length imaging is much longer and consequently, the workload for the operator and the burden on the subject increase.

Considering such circumstances, the object of the present invention is to provide an X-ray imaging device capable of cutting the time needed for the long-length image.

Means for Solving the Problem

The present invention constitutes the following structure to solve such problems.

Specifically, an X-ray imaging apparatus of the present invention comprises: an X-ray tube that irradiates an X-ray to a subject; an X-ray detector that detects the X-ray that transmits the subject and outputs a detection signal; an imaging system shifting means that shifts an imaging system further comprising: the X-ray source; and the X-ray detection means in the body-axis direction of the subject; an image generation element that generates a plurality of X-ray images based on the X-ray detection signal that the X-ray detection element outputs while the imaging system shifting means is shifting each of the imaging system; a reconstruction means that reconstructs a single long-length image by connecting said plurality of the X-ray images, which the image generation element generates, in the body-axis direction of the subject; an imaging system detection means that detects arbitrarily the present location of the imaging system consisting of the X-ray tube and the X-ray detector; a candidate point registration means that registers the predetermined location comprising both end of the long-length region as the candidate point; a start location determination means that determines the candidate point that is closer to the present location of the imaging system as the imaging start location that is the location of the imaging system when taking the first X-ray image, and the candidate point that is farther from the present location of the imaging system as the imaging end location that is the location of the imaging system when taking the last X-ray image; a determination directive means that directs the determination of the imaging start location and the imaging end location that the start location determination means determines.

Action and Effect

According to the X-ray imaging apparatus of the present invention, a candidate point registration means registers the predetermined location, which comprises both ends of the long-length region that is an imaging range of the long-length region, as the candidate point. The start location determination means that determines the candidate point, which is closer to the present location of the imaging system, as the imaging start location, and the candidate point, which is farther from the present location of the imaging system, as the imaging end location. The imaging start location is specifically the candidate point that is closer to the present location of the imaging system, so that the distance, in which the imaging system shifts to the imaging start location when the imaging of the X-ray image starts, can be cut. Therefore, the time needed for imaging the long-length image can be shortened.

In addition, the imaging system detection means detects as needed the present location of the imaging system, so that the candidate point as the imaging start location is updated to be the closer point to the present location of the imaging system every time when the determination directive means directs. Therefore, when the imaging of the long-length image is implemented multiple times, the determination directive means updates the candidate point to be the imaging start location following the end of the nth long-length imaging, so that the shift distance to the imaging start location of the imaging system can be cut when the (n+1)th long-length imaging starts. Accordingly, the determination directive means repeats the determination direction of the image start location and the long-length imaging so that the time needed to implement all long-length imagings multiple times can be largely cut. As results, the workload of the operator and the burden on the subject decrease and the work-flow of the long-length imaging can be improved.

According to the present invention set forth above, it is preferable that the X-ray imaging apparatus that the imaging system shifting means shifts the imaging system to the candidate point that the starting location determination means determines to be the imaging start location.

Action and Effect

According to the X-ray imaging apparatus of the present invention, the imaging system shift means shifts the imaging system to the candidate point that the starting location determination means determines to be the imaging start location. In such aspect, the determination directive means determines the directive, so that the candidate point, which is closer to the present location of the imaging system, is determined as the imaging start location and the imaging system shifts to the imaging start location. Specifically, the determination of the imaging start location and the shift to the imaging start location are executed as interlocked, so that the work that is the directive by which the imaging system shifts to the imaging start location can be eliminated. Therefore, the time needed to implement long-length imaging can be further shortened.

According to the present invention set forth above, it is preferable that the X-ray imaging apparatus further comprises a candidate point registration directive means that directs the candidate point registration means to register the present location of the imaging system.

Action and Effect

According to the X-ray imaging apparatus, the registration directive means that directs the candidate point registration means to register the present location of the imaging system. According to such aspect, the present location of the imaging system is registered as the candidate point. Therefore, the registration directive means directs following confirmation of that the location of the imaging system is actually adjusted and the present location of the imaging system is appropriate as the candidate point, so that the further appropriate location of both ends of the long-length region can be specified as candidate point. As results, the diagnostic capability of the long-length image can be further improved.

Effect of the Invention

Action and Effect

According to the X-ray imaging apparatus of the present invention, the candidate point registration means registers the predetermined location comprising both ends of the long-length region that is the imaging range of the long-length region as the candidate point, the start location determination means that determines the candidate point, which is closer to the present location of the imaging system, as the imaging start location, and the candidate point, which is farther from the present location of the imaging system, as the imaging end location. The imaging start location is specifically the candidate point that is closer to the present location of the imaging system, so that the distance, in which the imaging system shifts to the imaging start location when the imaging of the X-ray image starts, can be cut. Therefore, the time needed for imaging of the long-length image can be shortened.

In addition, the imaging system detection means detects as needed the present location of the imaging system, so that the candidate point as the imaging start location is updated to be the closer point to the present location of the imaging system every time when the determination directive means directs. Therefore, when the imaging of the long-length image is implemented multiple times, the determination directive means updates the candidate point to be the imaging start location following the end of the nth long-length imaging, so that the shift distance to the imaging start location of the imaging system can be cut when the (n+1)th long-length imaging starts. Accordingly, the determination directive means repeats the determination direction of the image start location and the long-length imaging so that the time needed to implement all long-length imagings multiple times can be largely cut. As a result, the workload of the operator and the burden on the subject decrease and the work-flow of the long-length imaging can be improved.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 1A is a schematic diagram illustrating the entire system of the X-ray imaging apparatus aspect of the Embodiment, and FIG. 1B is a block diagram illustrating the system of the X-ray imaging apparatus according to the aspect of the Embodiment.

FIG. 2A is the schematic view illustrating the aspect in which the start location determination means determines the imaging start location from the candidate point, and FIG. 2B is the schematic view illustrating a variety of switches installed to the input element.

FIG. 4A is a view illustrating the state in which one end of the long-length region is registered as the candidate point at the step S1, FIG. 4B is a view illustrating the state in which the other end of the long-length region is registered as the candidate point at the step S1, FIG. 4C is a view illustrating the state in which the imaging start location and the imaging end location are determined at the step S2, and FIG. 4D is a view illustrating the state in which the X-ray images are continuously taken at the step S4.

FIG. 5A-5D are schematic views illustrating an operation of the second long-length imaging according to the aspect of the Embodiment, FIG. 5A is a view illustrating the state before determining the imaging start location at the step S2A, FIG. 5B is a view illustrating the state after determining the imaging start location at the step S2A, FIG. 5C is a view illustrating the state in which the first X-ray image is taken at the step S4A, and FIG. 5D is a view illustrating the state in which the X-ray images are continuously taken at the step S4A.

FIG. 7A is a schematic view illustrating the entire system of the X-ray imaging apparatus according to the aspect of the conventional Embodiment, and FIG. 7B is a schematic view illustrating the input element of the X-ray imaging apparatus according to the aspect of the conventional Embodiment.

FIG. 9A is a schematic diagram illustrating a process of the step S1, and FIG. 9B is a schematic diagram illustrating the process of the step S2.

FIG. 10A is a view illustrating the process of the step S3 relative to the first imaging, FIG. 10B is a view illustrating the process of the step S4 relative to the first imaging, FIG. 10C is a view illustrating the process of the step S3 relative to the second imaging, and FIG. 10D is a view illustrating the process of the step S4 relative to the second imaging.

DETAILED DESCRIPTION OF THE PREFERRED EMBODIMENTS

Figure 1A:
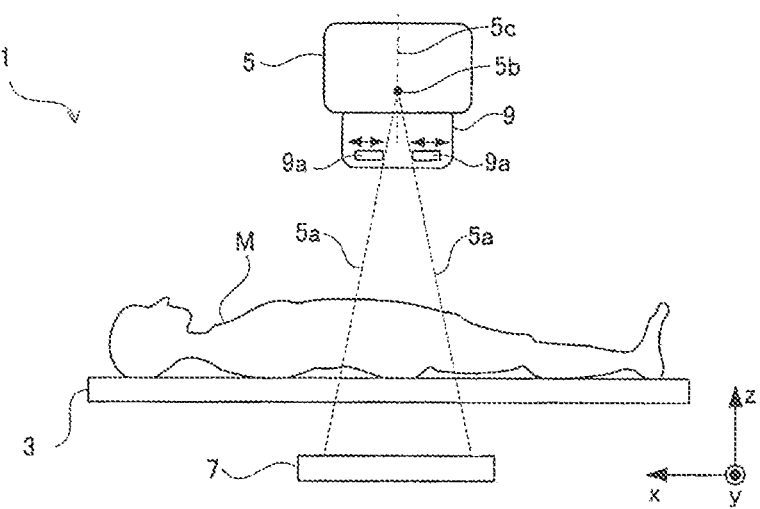
FIG. 1A, 1B are schematic views illustrating a structure of an X-ray imaging apparatus according to the aspect of the Embodiment.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

(Illustration of the Entire Structure)

Referring to FIG. 1A, an X-ray imaging apparatus according to the aspect of the Embodiment, comprises a tabletop 3 on which a subject M is in decubitus (lying down), 5a an X-ray tube 5 that irradiates an X-ray 5a to the subject M, and an X-ray detector 7 that detects the X-ray 5a that is irradiated toward and transmits through the subject M. The X-ray tube 5 and the X-ray detector 7 constitute an imaging system and are in-place facing to each other and sandwich the tabletop 3.

The X-ray detector 7 detects the X-ray, which is irradiated to the subject M from the X-ray tube 5 and transmits therethrough, and converts the detected X-ray to an electric signal and then outputs the electric signal as a detection signal. The X-ray detector 7 is such as a flat panel detector (FPD) and so forth. A collimator 9 that narrows the X-ray 5a to a pyramid-like shape is installed to the inferior part of the X-ray tube 5.

The collimator 9 comprises two board-like diaphragms (blocking board) 9a aligned in the x-direction (longitudinal direction of the tabletop 3 and the body-axis direction of the subject M). Each diaphragms 9a is made of a material that can shield (block) X-rays and the material therefor may include e.g., lead. According to the aspect of the Embodiment, it is given that each of a pair of the diaphragms 9a shifts mirror-image symmetrically in the x-direction so that the center axis 5c of the X-ray 5a irradiated from the X-ray focal point 5b of the X-ray tube 5 is the baseline.

Broadening of the X-ray 5a that is irradiated from the focal point 5b is narrowed (limited) by each diaphragm 9a to provide the pyramid-like shape. Then, the X-ray 5a passing through the aperture that is formed by each diaphragm 9a is irradiated to the subject M. Specifically, the aperture is adjusted by opening-and-closing each diaphragm 9a so that the location of the region (X-ray irradiation field) to which the X-ray 5a is irradiated and the range thereof are adjusted.

Figure 1B:
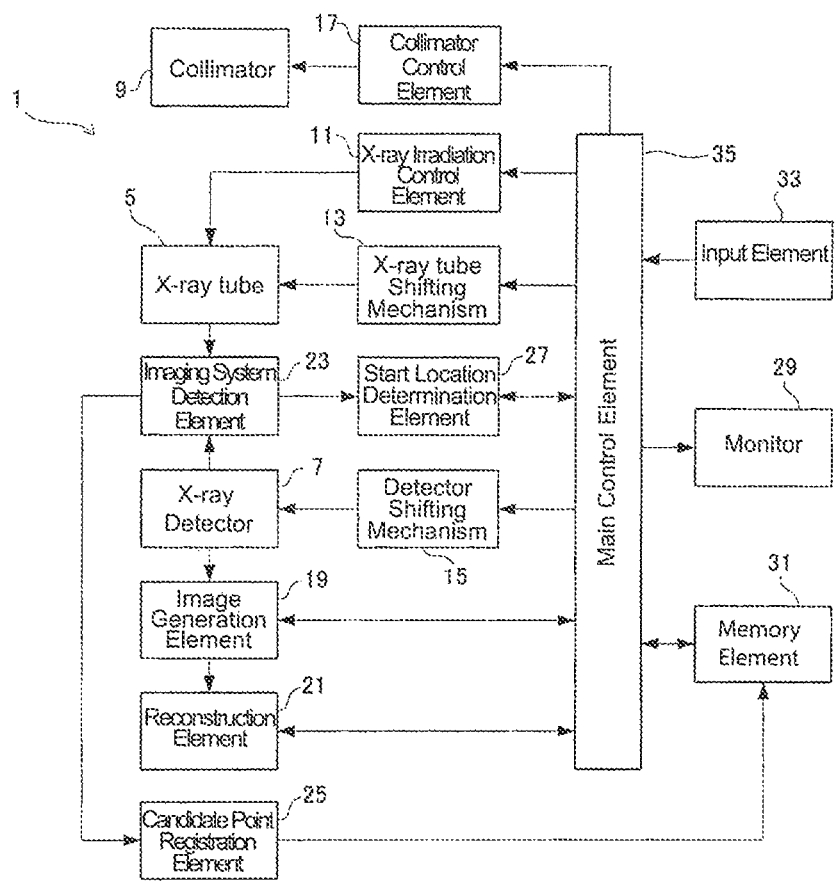

In addition, referring to FIG. 1B, the X-ray imaging apparatus 1 comprises an X-ray irradiation control element 11; an X-ray tube shifting mechanism 13; a detector shifting mechanism 15; a collimator control element 17; an image processing element 19; and a reconstruction element 21. The X-ray irradiation control element 11 that is connected to the X-ray tube 5 controls a dose of X-rays irradiated from the X-ray tube 5 and a timing of the X-ray irradiation and so forth by controlling a tube voltage and a tube electric current.

The X-ray tube shifting mechanism 13 that is connected to the X-ray tube 5 controls shifting the X-ray tube 5 in the x-direction. The detector shifting mechanism 15 that is connected to the X-ray detector 7 controls shifting of the X-ray detector in the x-direction. Specifically, the imaging system comprising the X-ray tube 5 and the X-ray detector 7 shifts synchronously in the x-direction according to controls of the X-ray tube shifting mechanism 13 and the detector shifting mechanism 15. In addition, the relative location of the imaging system to the table 3 (or the subject M) is called "imaging location". The X-ray tube shifting mechanism 13 and the detector shifting mechanism 15 correspond to the imaging system shift means of the present invention.

The collimator control element 17 controls opening, closing and shifting of each diaphragm 9a installed to the collimator 9. Specifically, the collimator 17 controls the location and the range of the X-ray irradiation field. The image generation element 19 that is installed to the latter part of the X-ray detector 7 generates an X-ray image based on the X-ray detection signal output from the X-ray detector 7. The reconstruction element 21 that is installed to the latter part of the image generation element 19 reconstructs the long-length image by connecting each X-ray image, which the image generation element 19 generates, in the x-direction.

The X-ray imaging apparatus 1 according to the aspect of the Embodiment further characteristically comprises the imaging system detection element 23, a candidate point registration element 25, and the start location imaging determination element 27. The imaging system detection element 23 that detects each coordinate location of the imaging system as needed comprises, for example, such as a potentiometer or an encoder and so forth. The candidate point registration element 25 registers two predetermined points as candidate points in the x-direction. The candidate point that is the location of a coordinate location that is a candidate to be an imaging start location or the imaging end location corresponds specifically to the end of the long-length region in the x-direction. The imaging system detection element 23 corresponds to the imaging system detection means of the present invention, and the candidate point registration element 25 corresponds to the candidate point registration means of the present invention.

According to the aspect of the Embodiment, the candidate point registration element 25 registers the present location of the imaging system which the imaging system detection element 23 detects according to the operation of the candidate point registration switch set forth later. In such aspect, the location of the appropriate candidate point can be specified more accurately as the end of the long-length region by visually and comparatively referring to the imaging location at which the imaging system actually locates and the location at which the subject M is loaded on the table 3.

The start location determination element 27 determines the imaging start location and the imaging end location using the candidate point that is registered, based on the distance between the present location of the imaging system and each coordinate location of the candidate point that the candidate point registration element 25 registers. The imaging start location is the imaging location of the first X-ray image of the X-ray images that are taken to reconstruct the long-length image. The imaging end location is the imaging location at which the last X-ray image is taken. The imaging start location determination element 27 corresponds to the start location determination means of the present invention.

Now, the inventor sets forth the mechanism by which the start location determination element 27 determines the imaging start location and the imaging end location. The start location determination element 27 determines the candidate point, which is closer to the present location of the imaging system, as the imaging start location, and the candidate point, which is far from the present location of the imaging system, as the imaging end location. Specifically, referring to FIG. 2A, the present location of the imaging system is Ln, and each location of registered candidate points is Lx and Ly.

Figure 2A:
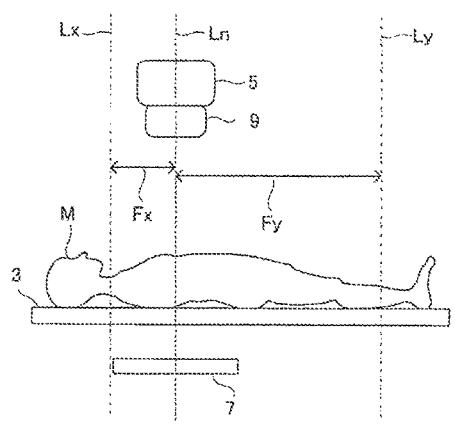
FIG. 2A, 2B are schematic views illustrating a structure of an X-ray imaging apparatus according to the aspect of the Embodiment.

In such case, the start location determination element 27 compares the distance Fx between the present location Ln of the imaging system and the candidate point Lx and the distance Fy between the present location Ln of the imaging system and the candidate point Ly. Referring to FIG. 2A, when the distance Fx is shorter than the distance Fy, the start location determination element 27 determines that the candidate point Lx is the imaging start location, and that the candidate point Ly is the imaging end location. Reversely, when the distance Fx is longer than the distance Fy, the start location determination element 27 determines that the candidate point Ly is the imaging start location, and that the candidate point Lx is the imaging end location.

The present location of the imaging system (imaging location at the present time) is detected as needed by the imaging system detection element 23, and the registered location of the candidate point is stored in the memory element 31. Therefore, the start location determination element 27 determines the imaging start location and the imaging end location based on the distance between the present location of the imaging system and the coordinate location of the candidate point.

Referring to FIG. 1B, The X-ray imaging apparatus 1 further comprises a monitor 29, the memory storing element 31, an input element 33 and a main control element 35. The monitor 29 displays a variety of images such as the X-ray image that the image generation element 19 generates, and a long-length image that the reconstruction element 21 reconstructs, and so forth. The memory element 31 stores a variety of data of such as the X-ray image that the image generation element 19 generates, and a long-length image that the reconstruction element 21 reconstructs, and the coordinate location of the candidate point that the candidate point registration element 25 registers.

The input element 33 to which an operator inputs a directive is e.g., a panel for a keyboard input and a panel for a touch-panel input and so forth. The main control element 35 that comprises a central processing unit (CPU) and so forth controls comprehensively the X-ray irradiation control element 11, the X-ray tube shifting mechanism 13, the detector shifting mechanism 15, the collimator 17, the image generation element 19, the reconstruction element 21, the candidate point registration element 25, and the start location determination element 27 and so forth based according to the content input into the input panel 33.

Figure 2B:
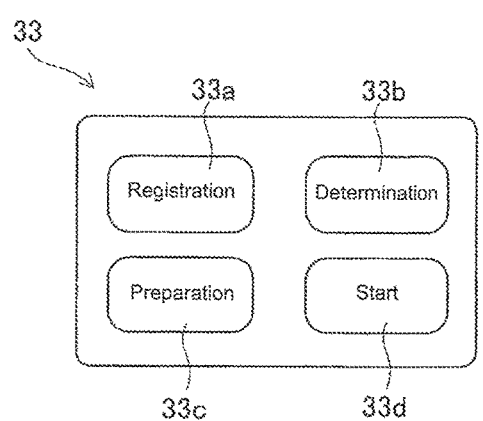

Referring to FIG. 2B, the input element 33 comprises a candidate point registration switch 33a, a start location determination switch 33b, an imaging preparation switch 33c, and an imaging start switch 33d in addition to the aspect by which a variety of directives is input. The candidate point registration switch 33a connects the candidate point registration element 25 via the main control element 35 and directs the candidate point registration through the candidate point registration element 25. Specifically, the candidate point registration element 25 is operative by operating the candidate point registration switch 33a and the candidate point is registered thereby. The candidate point registration switch 33a corresponds to the registration directive means of the present invention.

The start location determination switch 33b that connects the start location determination element 27 via the main control element 35 directs the determination of the imaging start location and the imaging end location by the start location determination element 27. Specifically, the start location determination element 27 that is operative by operating the start location determination switch 33b determines the imaging start location and the imaging end location based on the distance between the present location of the imaging system and each registration point. The start location determination switch 33b corresponds to the determination directive means of the present invention.

The imaging preparation switch 33c that connects the X-ray tube shifting mechanism 13 and the detector shifting mechanism 15 and so forth via the main control element 35 directs the imaging preparation for a series of the X-ray images that construct the long-length image. Each of the imaging system shifts to the imaging start location by operating the imaging preparation switch 33c and a variety of operations relative to the imaging preparation of the X-ray image is operative thereby. The imaging start switch 33d that connects the X-ray irradiation control element 11 and so forth via the main control element 35 directs to start imaging a series of the X-ray images. The X-ray tube 5 starts to irradiate an X-ray by operating the imaging start switch 33d. Relative to the aspect to operate each of switches 33a-33d, a method for selecting an operation by a mouse and so forth by displaying on the graphical user interface (GUI) in addition to the method in which a button is pressed down and any known method can be applied as needed.

Description of the Operation

Figure 3:
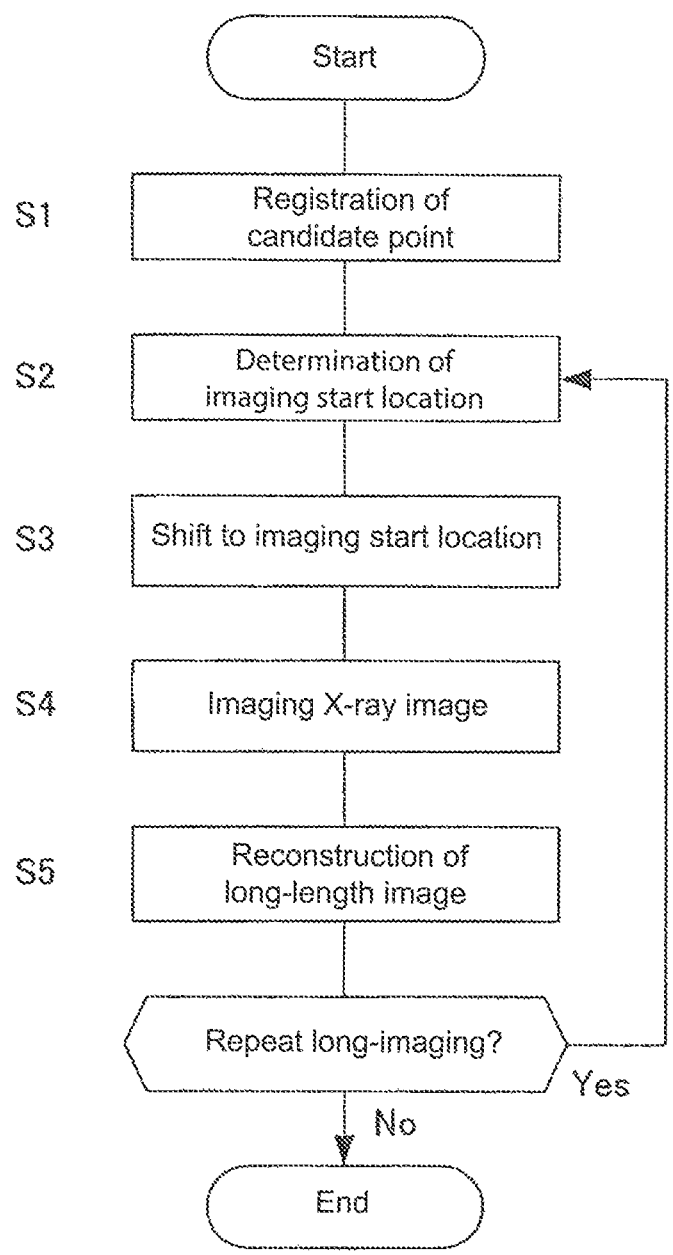
FIG. 3 is a flow chart illustrating operation steps of the X-ray imaging apparatus of according to the aspect of the Embodiment.

Next, the inventor sets forth the operation of the X-ray imaging apparatus 1 according to the aspect of the Embodiment. FIG. 3 is a flow chart illustrating an operation of the X-ray imaging apparatus according to the aspect of the Embodiment. Now, the inventor sets forth the summary of the operation of the X-ray imaging apparatus, for example, such as the long-length imaging that targets the long-length region, as a imaging target subject, in the body-axis direction of the subject. In addition, as set forth later, it is given that the subject is subject to one long-length imaging of each of the supine posture and the lateral decubitus posture. Specifically, the two long-length imagings are implemented according to the aspect of the Embodiment.

Step S1 (Registration of the Candidate Point)

Figure 4A:
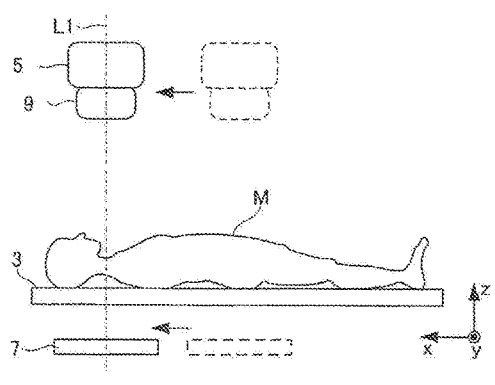
FIG. 4A-4D are schematic views illustrating an operation of the first long-length imaging according to the aspect of the Embodiment.

When the long-length imaging is implemented, first the subject M is loaded on the table 3 and takes a supine posture. And the candidate point is registered to determines the long-length region that is a target of the long-length imaging. As set forth above, the candidate point that is the location of the coordinate location that is a candidate to be an imaging start location or the imaging end location, i.e., the location to be the end of the long-length region in the x-direction. The operator shifts each of the imaging system, consisting of the X-ray tube 5 and the X-ray detector 7, to the appropriate location as the one end of the long-length region while making sure the locational relationship between the subject M and the imaging system. In addition, referring to FIG. 4A, the appropriate location as one end of the long-length image is L1. In such case, the operator shifts each imaging system from the initial location indicated by the broken line to the location L1 indicated by the solid line referring to FIG. 4A by the own operation.

The operator activates the candidate point registration element 25 by operating the candidate point registration switch 33a following making sure e.g., by eyes that the present location of the imaging system is appropriate as the one end of the long-length region. The candidate point registration element 25 is activated so that the location L1 that is the present location of the imaging system is registered as the first candidate point. The coordinate data relative to the registered location L are sent to the memory element 31 to be stored.

Figure 4B:
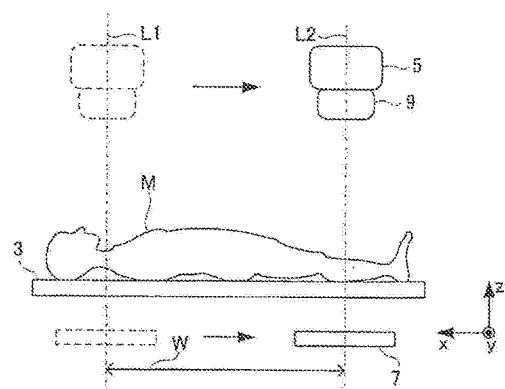

Next, the operator determines the location coordinate of the other end of the long-length region following registering the location coordinate of the one end of the long-length region. The operator shifts each of the imaging system to the appropriate location as the other end of the long-length region while making sure the locational relationship between the subject M and the imaging system. In addition, referring to FIG. 4B, the appropriate location as the other end of the long-length image is L2. In such case, the operator shifts each of the imaging system from the initial location L1 indicated by the broken line to the location L2 indicated by the solid line referring to FIG. 4B by the own operation.

The operator activates the candidate point registration element 25 by operating the candidate point registration switch 33a following making sure that the present location of the imaging system is the appropriate location as the other end of the long-length region. The candidate point registration element 25 is activated so that the location L2 that is the present location of the imaging system is registered as the second candidate point. The coordinate data relative to the registered location L2 are sent to the memory element 31 to be stored. The location coordinates of the two candidate points are respectively registered so that the long-length range W is specified and the process of the step S1 ends.

Step S2 (Determination of the Imaging Start Location)

The imaging start location determination is implemented following registration of the location coordinate data of the candidate point. Specifically, the operator activates the start location determination element 27 by operating the start location determination switch 33b following completion of the registration of the candidate points L1 and L2. The start location determination element 27 is operative so that one candidate point of registered candidate points L1 and L2, which is closer to the present location of the imaging system, is determined as the imaging start location. On the other hand, the candidate point which is farther from the present location of the imaging system is determined as the imaging end location.

Figure 4C:
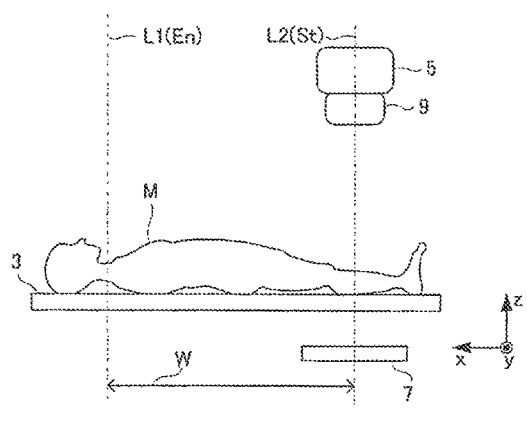

At the step S1, lastly the imaging system is shifted to the location L2 and the candidate point is registered. Therefore, in general, the present location of the imaging system coincides approximately with the location of the candidate point L2 when the start location determination switch 33b is operative at the step S2. Specifically, the candidate point L2 of the candidate points L1 and L2 is closer to the present location of the imaging system. Accordingly, the candidate point L2 is determined as the imaging start location St, and the candidate point L1 is determined as the imaging end location En (referring to FIG. 4C).

In addition, when the imaging system shifts to the proximity of the candidate point L1 of the imaging system after the location L2 is registered as the candidate point at the step S1, the candidate point L1 is closer to the present location of the imaging system. In such case, the start location determination switch 33b is operative so that the candidate point L1 is determined as the imaging start location St. and the candidate point L2 is determined as the imaging end location En. In such way, every time when the determination is executed, the location data of the imaging start location St is updated as the location data of the candidate point that is closer to the present location of the imaging system.

Accordingly, the determination of the imaging start location is executed prior to the preparation relative to the step S3 set forth later, so that the shift distance of the imaging system at the step S3 can be shorter. According to the Embodiment, it is given that the imaging system does not shift following completion of the step S1, and the candidate point L2 is determined as the imaging start location St. The start location determination element 27 determines the imaging start location and the imaging end location, so that the process at the step S2 ends.

Step S3 (Shift Toward the Imaging Start Location)

The operator prepares the X-ray imaging by operating the imaging preparation switch 33c following determination of the imaging start location. Each of the imaging system shifts to the location that is determined by operating the imaging preparation switch 33c as the imaging start location L2 and a variety of operations relative to the imaging preparation of the X-ray image is operative thereby (referring to FIG. 4C).

An operation relative to the imaging preparation is e.g., an adjustment of the X-ray irradiation field with the collimator 9 and so forth. Specifically, when the imaging preparation switch 33c is operative, the main control element 35 sends the control signal to the collimator control element 21. The collimator control element 21 shifts the diaphragm 9a, which is installed to the collimator 9, in the x-direction in accordance with the content of the control. The diaphragm 9a adjusts the X-ray irradiation field of the X-ray 5a to become a rectangular region having the width T in the x-direction. In addition, the operator operates the input element 33 as needed to input the imaging conditions, such as a tube voltage and a tube electric current and so forth.

According to the aspect of the Embodiment, the start location determination element 27 determines one of the candidate points, which is closer to the present location of the imaging system, as the imaging start location. Therefore, the shift distance of the imaging system at the step S3 is shorter, so that the time needed for the step S3 is shorter. Relative to the step according to the aspect of the Embodiment, in general, the coordinate location of the imaging system at the step S2 and L2 is determined as the imaging start location are approximately the same as each other. Accordingly, the imaging system needs to barely shift at the step S3. Accordingly, the time needed for the imaging system to shift is approximately zero at the step S3. The imaging system shifts to the imaging start location St, i.e., the candidate point L2, and then the imaging preparation is completed, so that the step relative to the step S3 ends.

Step S4 (Imaging of an X-Ray Image)

Figure 4D:
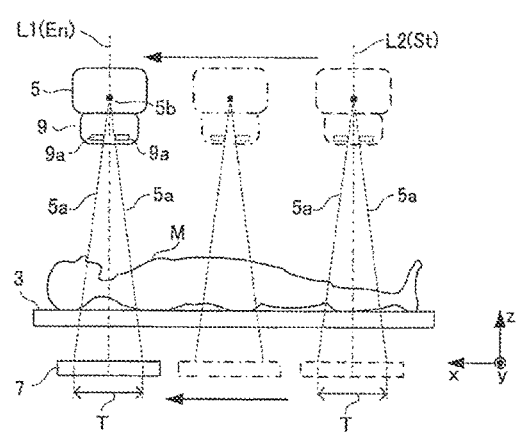

The operator images the X-ray image by operating the imaging start switch 33d following completion of the X-ray imaging preparation for an X-ray image. The X-ray irradiation control element 11 adds the high-voltage to the X-ray tube 5 by operating the imaging start switch 33d so that the X-ray 5a is irradiated from the X-ray tube 5 (referring to FIG. 4D). The X-ray detector 7 detects the X-ray 5a that transmits through the subject M and outputs an X-ray detection signal. The image generation element 19 generates the X-ray image having the width T in the x-direction based on the X-ray detection signals.

And the X-ray tube shifting mechanism 13 and the detector shifting mechanism 15 shift synchronously each of the imaging system in the x-direction in accordance with the control signal that the main control element 35 outputs. Specifically, referring to FIG. 4D, the X-ray tube 5 and the X-ray detector 7 shift to the imaging end location En (location L1) indicated by the broken line via the location indicated by the dashed-two dotted line from the imaging start location St (location L2) indicated by the solid line.

And every time when each of the imaging system shifts the distance corresponding to the width T of the X-ray image in the x-direction, the X-ray tube 5 repeats the irradiation of the X-ray 5a according to the control given by the X-ray irradiation control element 11. Every time when the X-ray 5a is irradiated, the X-ray image, in which each of the imaging location is the center, is generated. In such way, a plurality of the X-ray images having the width T in the x-direction relative to the range of the long-length region W from the location L1 to the location L2 is generated. Each of the imaging system shifts to the imaging end location En and each X-ray image comprising the long-length region W is generated, by which the process relative to the step S4 ends.

Step S5 (Reconstruction of a Long-Length Image)

The long-length image is reconstructed following completion of an imaging of the X-ray image. Specifically, the reconstruction element 21 connects each X-ray image, which the image generation element 19 generates, in the body-axis direction of the subject M to reconstruct the single long-length image. The reconstructed long-length image Q1 is displayed on the monitor 29 and in addition, stored in the memory element 31. In such way, the single long-length image Q1 imaging the subject M in the supine posture is acquired relative to the long-length region W. The long-length image is reconstructed, so that the process relative to the step S5 ends.

Following completion of the step S5, the operator determines whether repeats the long-length imaging or not, and diverges the processing. When repeats the long-length imaging, the operator returns to the step S2 and continues the processing. When the imaging ends, the operator operates the input element 35 as needed and the entire processes relative to the long-length imaging end. Relative to the long-length region W according to the aspect of the Embodiment, the long-length imaging is implemented on the subject M in the lateral decubitus posture relative to the same long-length region W following the long-length imaging relative to the subject M in the supine posture. Accordingly, the step returns to the step S2 following acquisition of the long-length image Q1 and the processes of the steps S2-S5 are executed again. In addition, the processes of the steps S2-S5 at the second time are the steps S2A-S5A with the additional sign A to distinguish from the steps S2-S5 at the first time.

Step S2A (Determination of the Imaging Start Location)

Figure 5C:
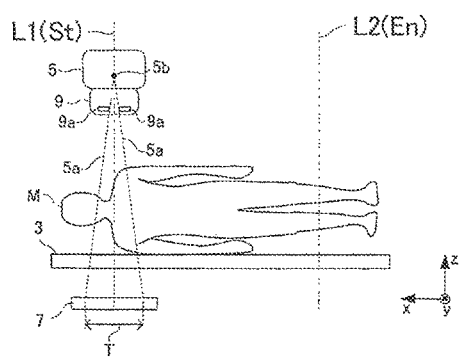

The posture of the subject M is changed from the supine posture to the lateral decubitus posture following acquisition of the long-length image Q imaging the subject M in the supine posture (referring to FIG. 5A). Then the operator determines the imaging start location by operating the start location determination switch 33b following changing of the posture of the subject M. The start location determination element 27 is operative by operating the start location determination switch 33b so that one candidate point of registered candidate points L1 and L2, which is closer to the present location of the imaging system, is determined as the imaging start location.

The imaging system shifts from the location L2 to the location L1 at the step S4, so that the candidate point L1, when comparing the candidate point L1 with the candidate point L2, is closer to the present location of the imaging system when at the step S2A. Accordingly, the start location determination switch 33b is operative so that the candidate point L1 is determined as the imaging start location St at the step S2A, and the candidate point L2 is determined as the imaging end location En (referring to FIG. 5B). Specifically, the start location determination element 27 is operative so that the setup of the imaging start location St and the imaging end location En is changed in accordance with the present location of the imaging system.

Step S3A (Shift Toward the Imaging Start Location)

The operator prepares the X-ray imaging by operating the imaging preparation switch 33c following determination of the candidate point L1 that is the imaging start location St. Each of the imaging system shifts to the location L1 that is determined as the imaging start location by operating the imaging preparation switch 33c and a variety of operations relative to the imaging preparation of the X-ray image is operative thereby. The imaging system has shifted already to the location L1 when the step S4 ends, so that the time needed for the imaging system to shift to the imaging start location St at the step S3A is largely shortened (referring to FIG. 5B).

Step S4A (Imaging of an X-Ray Image)

The operator images the X-ray image by operating the imaging start switch 33d following a completion of the X-ray imaging preparation for an X-ray image. The X-ray irradiation control element 11 adds the high-voltage to the X-ray tube 5 by operating the imaging start switch 33d so that the X-ray 5a is irradiated from the X-ray tube 5 (referring to FIG. 5C). The X-ray detector 7 detects the X-ray 5a that transmits through the subject M and outputs an X-ray detection signal. The image generation element 19 generates the X-ray image having the width T in the x-direction based on the X-ray detection signals.

Figure 5D:
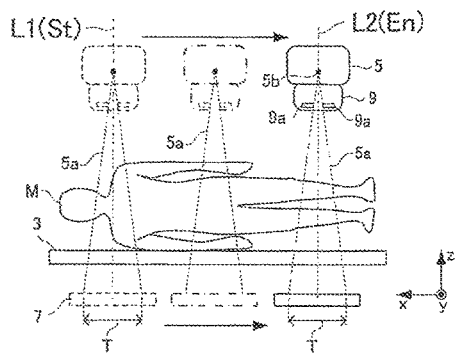

And, referring to FIG. 5D, the X-ray tube 5 and the X-ray detector 7 shift to the imaging end location En (location L2) indicated by the broken line via the location indicated by the dashed-two dotted line from the imaging start location St (location L1) indicated by the solid line. And every time when each of the imaging system shifts the same distance as the width T of the X-ray image in the x-direction, the X-ray tube 5 repeats the irradiation of the X-ray 5a according to the control given by the X-ray irradiation control element 11. In such a way, a plurality of the X-ray images having the width T in the x-direction relative to the range of the long-length region W from the location L1 to the location L2 is generated.

Step S5A (Reconstruction of a Long-Length Image)

The reconstruction element 21 connects each X-ray image, which the image generation element 19 generates, in the body-axis direction of the subject M to reconstruct the single long-length image following the imaging end of the X-ray image. The reconstructed long-length image Q2 is displayed on the monitor 29 and in addition, stored in the memory element 31. In such way, the single long-length image Q2 imaging the subject M in the lateral decubitus posture is acquired relative to the long-length region W. The long-length images Q1 and Q2 are acquired, so that all steps relative to the long-length imaging end.

Effects of the Aspect of the Embodiment

According to the aspect of the Embodiment, the time needed for long-length imaging is largely shortened. According to the conventional aspect, when the range of the long-length region W is determined, one end L1 of the long-length region W is registered as the imaging start location and the other end L2 of the long-length region is registered as the imaging end location.

According to the aspect of the conventional X-ray imaging apparatus, the set-up of the imaging start location is fixed to the location L1 and the setup of the imaging end location is fixed to the location L2 regardless the location of the imaging system unless the registered location data are canceled and re-registered. Therefore, even when the present location of the imaging system is far from the location L1 and closer to the location L2, the imaging system must shift a long distance to the location L1 that is specified as the imaging start location (the step S3, referring to FIG. 8) at the step of the preparation step for the X-ray imaging.

Figure 6A:
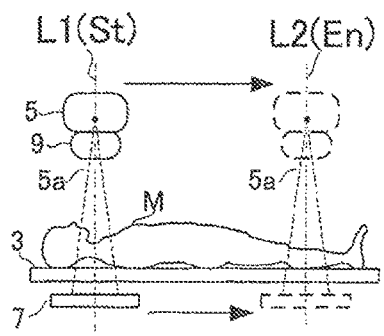
FIGS. 6A-6F are views illustrating the comparison between the conventional Embodiment (FIGS. 6A-6C) and the present Embodiment (FIGS. 6D-6F) relative to the operation of the X-ray imaging apparatus, by which the long-length imaging is implemented multiple times.

As a result, when the long-length imagings are implemented multiple times relative to the same long-length region according to the conventional aspect, the imaging system must shift from the imaging end location to the imaging start location every time when the long-length imaging is implemented. Specifically, the n-times long-length imagings are executed by shifting the location L1, which is registered as the imaging start location St, to the location L2, which is registered as the imaging end location En (referring to FIG. 6A).

Figure 6B:
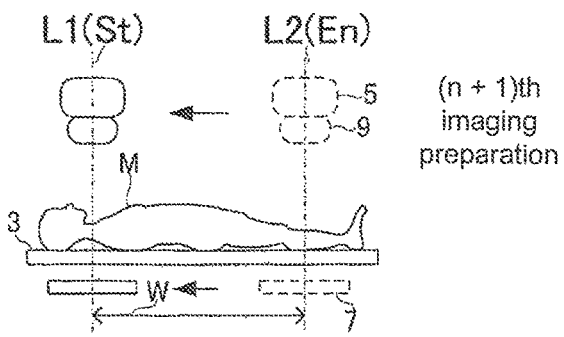

According to the conventional Embodiment, the setting of once registered imaging start location St and imaging end location En is fixed. Accordingly, the imaging system must shift from the location L2 as the imaging end location En to the location L1 as the imaging start location St at the preparation step for the (n+1)th long-length imaging following implementation of the nth long-length imaging (referring to FIG. 6B).

Figure 6C:
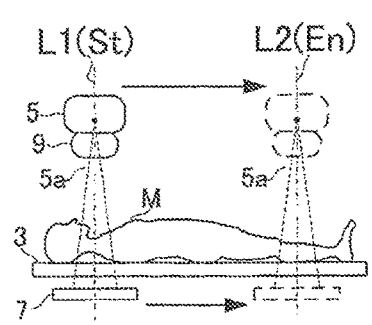
Figure 8:
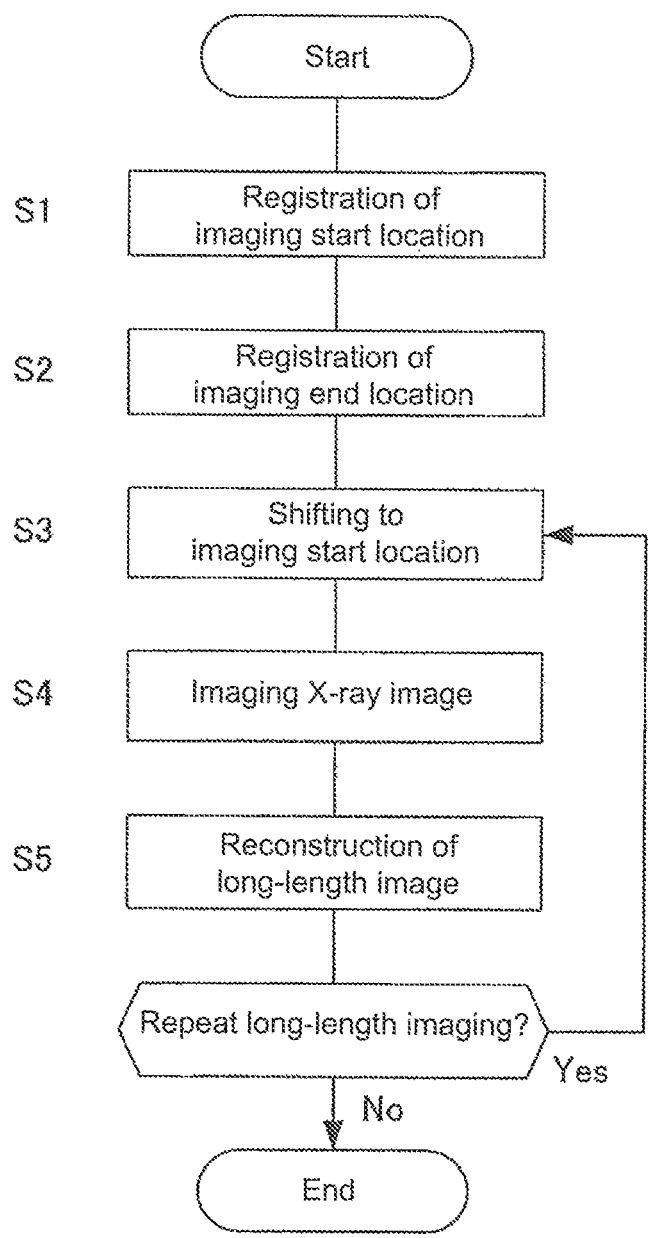
FIG. 8 is a flow chart illustrating operation steps of the X-ray imaging apparatus of according to the aspect of the conventional Embodiment.
Figure 9A:
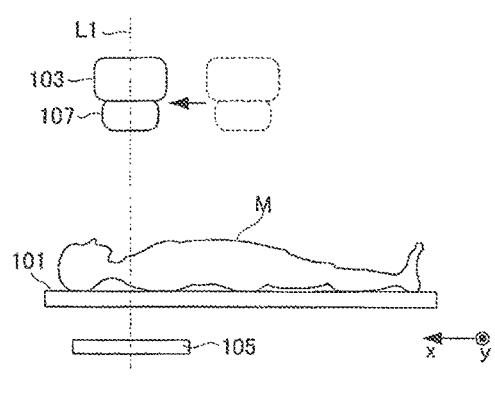
FIG. 9A, 9B are schematic diagrams illustrating operations of the step S1 and the step S2 according to the aspect of the conventional Embodiment.
Figure 9B:
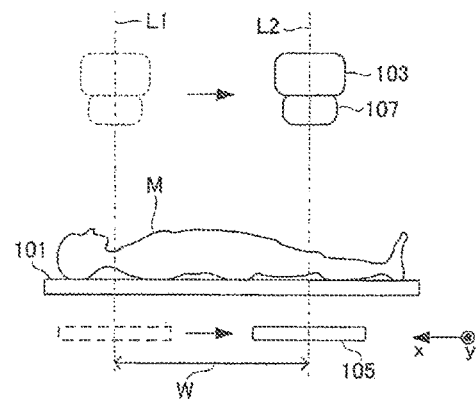
Figure 10A:
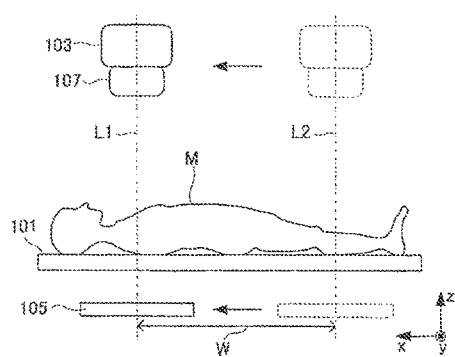
FIG. 10A-10D are schematic views illustrating an operation of the long-length imaging multiple times according to the aspect of the conventional Embodiment.
Figure 10B:
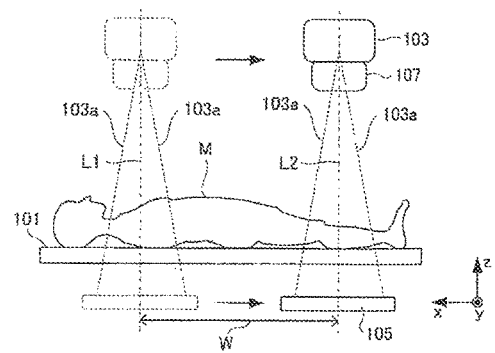
Figure 10C:
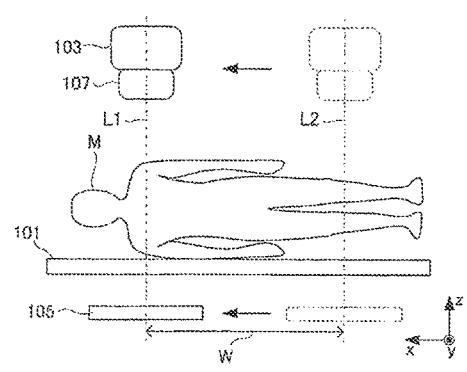
Figure 10D:
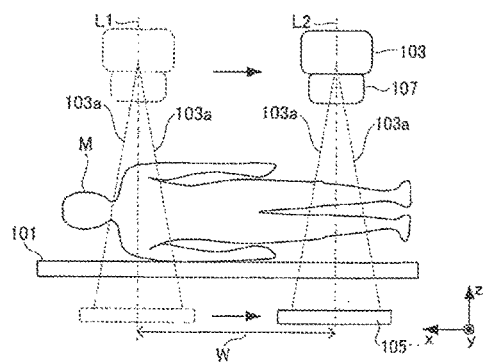

And the imaging of the X-ray image starts and an imaging of a series of the X-ray images is implemented while shifting from the location L1 as the imaging start location St to the location L2 as the imaging end location En so that the (n+1) times long-length imaging is completed (referring to FIG. 6C). Accordingly, when the long-length imaging is implemented n-times according to the conventional apparatus, the steps S3-S5 referring to FIG. 8 are repeated n-times and as results, the imaging system must shift back-and-forth at least (2n−1)/2 times between the location L1 and the location L2). Further, relative to the step S1 and the step S2, when considering the registration of the imaging start location and the imaging end location by shifting the imaging system to the actual locations L1 and L2, the imaging system shifts back-and-forth (2n+1)/2 times to implement n-times of the long-length imaging.

Therefore, according to the conventional aspect, the long-length imaging is repeated, so that the imaging system spends time for back-and-forth shifting. While imaging a series of the X-ray images, the subject must keep the same posture to prevent deformation of the X-ray images, so that physical and mental burdens of the subject increases due to the longer imaging time. In addition, the workload for the operator increases due to the longer imaging time and the long-length imaging work-flow efficiency decreases.

On the other hand, the X-ray imaging apparatus 1 according to the aspect of the Embodiment registers the end of the long-length region as the candidate point, and determines the imaging start location using the candidate point by operating the start location determination switch 33b. And, the determination of the imaging start location is implemented based on the distance between the present location of the imaging system and each candidate point. Specifically, the candidate point closest to the present location of the imaging system is determined as the imaging start location, so that the distance, which the imaging system shifts to the imaging start location at the preparation step relative to the step S3, is shorter.

In addition, the candidate point as the imaging start location is updated to be the candidate point that is closer to the present location of the imaging system every time when the start location determination switch 33b directs. Therefore, when the imaging of the long-length image is implemented multiple times, the start location determination switch 33b updates the candidate point to be the imaging start location following the end of the nth long-length imaging, so that the shift distance to the imaging start location of the imaging system can be cut when the (n+1)th long-length imaging is prepared. Accordingly, the start location determination switch 33b repeats the determination directive of the imaging start location and the long-length imaging, so that the time needed to implement the long-length imagings multiple times can be largely cut.

Figure 6D:
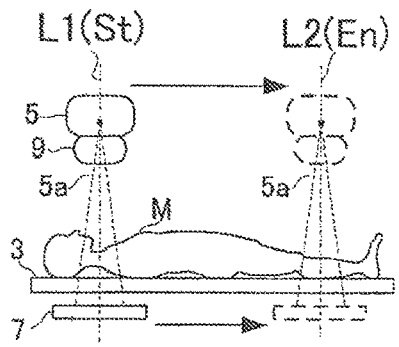

Specifically, the nth long-length imaging is executed by shifting the location L1, which is registered as the imaging start location St, to the location L2, which is registered as the imaging end location En (referring to FIG. 6D). Then, when the (n+1)th long-length imaging is implemented following the nth long-length imaging, the start location determination element 27 is operative at the step S2 to determine the imaging start location.

When the nth long-length imaging ends, the present location of the imaging system approximately coincides with the location L2, so that the start location determination element 27 determines the location L2 as the imaging start location St and determines the location L1 as the imaging end location En. Therefore, the simple operation, in which the start location determination switch 33b is operative, can update the location data of the imaging start location. Specifically, the setting state of the imaging start location and the imaging end location changes from the state, in which the location L1 is the imaging start location St and the location L2 is the imaging end location En, to the state, in which the location L1 is the imaging end location En and the location L2 is the imaging start location St.

Figure 6E:
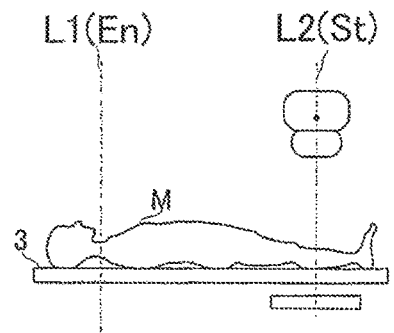
Figure 6F:
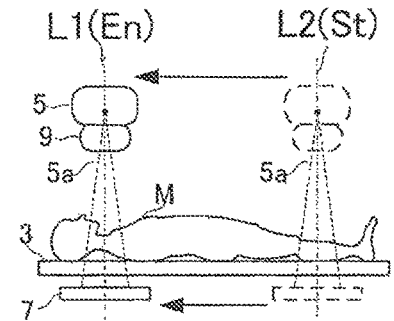
Figure 7A:
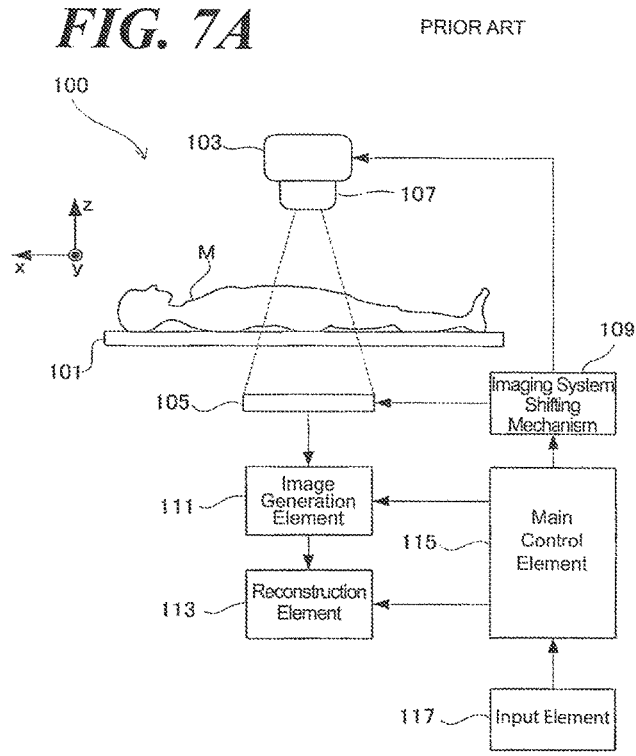
FIG. 7A, 7B are schematic views illustrating a structure of an X-ray imaging apparatus according to the aspect of the conventional Embodiment.
Figure 7B:
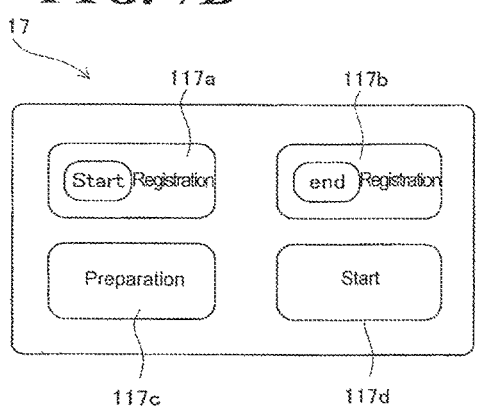

The shift destination of the imaging system is the imaging start location St, i.e., the location L2, at the imaging preparation step relative to the step S3. Accordingly, the determination of the imaging start location is executed at the step S2, so that the shift distance of the imaging system at the step S3 can be almost zero (referring to FIG. 6E). And the imaging of a series of the X-ray images is implemented while shifting from the location L2 as the imaging start location St to the location L1 as the imaging end location En, so that the (n+1)th long-length imaging is completed (referring to FIG. 6F).

In such way, according to the aspect of the Embodiment; the process at which the candidate point that is closest to the present location of the imaging system is determined as the X-ray image imaging start location, and the process at which the long-length image is reconstructed by imaging the X-ray images, are repeated under the state in which the locations of both ends of the long-length image are registered as the candidate points. Therefore, when the n-times long-length imagings are implemented using the X-ray imaging apparatus 1 according to the aspect of the Embodiment, the imaging system can reduce the number of the back-and-forth shift between the location L1 and the location L2 to (n/2)-times. In addition, at the step S1, even given the candidate point is registered by shifting the imaging system to the actual location L1 and the actual location L2, the back-and-forth shifting the imaging system is just [(n+1)/2] times at last.

The shift distance of the imaging system relative to the long-length imaging becomes shorter, so that the time needed for such shifting the imaging system can be cut. The setting change of the imaging start location St and the imaging end location En using the determination of the imaging start location is executed by the simple operation, in which just the start location determination switch 33b is operative, the time needed for the setting change of e.g., the imaging start location St is extremely short. Therefore, according to the aspect of the Embodiment, the time needed to execute the entire steps for the long-length imaging can be largely cut when particularly, the long-length imaging is repeated multiple times. As results, the burden on the subject due to keeping the posture thereof decreases, the workload of the operator decreases, and further, the work-flow of the long-length imaging can be greatly improved.

The present invention is not limited to the aspect of the Embodiments set forth above and another alternative Embodiment can be implemented set forth below.

(1) According to the aspect of the Embodiment set forth above, the step of determining the imaging start location at the step S2 and the step of shifting the imaging system to the imaging start location at the step S3 can be interlocked and implemented. Specifically, the start location determination switch 33b at the step S2 is operative, so that which one of the candidate point L1 and the candidate point L2 is closer to the present location of the imaging system is determined as the imaging start location St, and each of the imaging system shifts to the candidate point that is determined as the imaging start location St.

According to the aspect of the alternative Embodiment, the imaging preparation of the X-ray image is carried out automatically following finish of the determination of the imaging start location, so that the imaging preparation switch 33c can be eliminated. In such case, the input element 33 can be downsized. In addition, the step of operating the imaging preparation switch 33c can be skipped, so that the time needed for the long-length imaging can be further cut and in addition, the work-load of the operator can be further reduced.

(2) According to the aspect of the Embodiment set forth above, the inventor sets forth the case in which the long-length imaging is implemented for the decubitus (lying down) subject M in such supine posture or lateral decubitus posture, but the structure of the X-ray imaging apparatus 1 according to the aspect of the Embodiment can be also applied to the long-length imaging of the subject M in the standing posture. In such case, the body-axis direction of the subject M that is in parallel to the x-direction becomes in parallel to the vertical direction (z-direction). In addition, the structure in which the table 3 varies from the horizontal state to the vertical state can be applied thereto. In such case, the state of the table 3 is changed as needed, so that both supine posture and standing posture are acceptable to the X-ray imaging.

In addition, when the long-length imaging is implemented in the standing posture, the subject M has an illness or an injury in such as the lower leg and so forth in many cases. Specifically, in such case, the time needed for the long-length imaging must be strongly cut to reduce the burden of the subject M. The burden of the subject M can be largely cut using the X-ray imaging apparatus according to the aspect of the Embodiment, and particularly, when the long-length imagings of the subject in the standing posture are implemented multiple times.

(3) According to the aspect of the Embodiment, each of the X-ray tube 5 and the X-ray detector 7 transfer synchronously in the x-direction, but when the irradiation field of the X-ray 5a varies in the x-direction, the imaging system is not limited to the aspect in which the imaging system transfers synchronously. Another Embodiment in which the irradiation field of the X-ray 5a varies in the x-direction is the aspect disclosed in such as Patent Document 2, in which the X-ray detector 7 shifts in the x-direction while the X-ray tube 5 is rotating around the axis in the y-direction.

(4) According to the aspect of the Embodiment, each of the X-ray tube 5 and the X-ray detector 7 shifts in the x-direction followed by shifting the imaging location, but the table shifting mechanism not shown in FIG. can shift the table 3 in the x-direction. In such case, the relative location (imaging location) of each of the imaging system relative to the subject M displaces in the x-direction as interlocked with the shifting the table 3. Therefore, the irradiation field of the X-ray 5a displaces in the x-direction in accordance with the shifting the table 3.

(5) According to the aspect of the Embodiment set forth above, each diaphragm 9a is not limited to shift mirror-symmetrically, and may shift independently. In addition, the number of diaphragm 9a that the collimator 9 comprises can be changed as needed. For example, a pair of the diaphragms 9a that shifts vertically in the x-direction, and a pair of the diaphragms 9a that shifts horizontally in the y-direction (transverse direction of the table 3) orthogonal to the x-direction can be applied.

As used herein, an electronic or computer-type system may include, without limitation, an input device for receiving data in a tangible form (e.g., data feed, data signals, etc.), an output device for outputting data in tangible form (e.g. data feed, data signals, printing or displaying on a computer screen), a memory for storing data as well as computer code, and a processor (micro or otherwise) for executing computer code wherein said computer code resident in said permanent memory will physically cause said microprocessor to read-in data via said input device, process said data within said microprocessor and output said processed data via said output device.

It will be further understood by those of skill in the art that the apparatus and devices and the elements herein, without limitation, and including the sub components such as operational structures, circuits, communication pathways, elements, portions, control and calculating elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray imaging apparatus, computer and operational controls and technologies of radiographic devices and all their sub-components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical; e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

REFERENCE OF SIGNS

1 X-ray imaging apparatus
3 Tabletop
5 X-ray tube
7 X-ray detector
11 X-ray irradiation control element
13 X-ray tube shifting mechanism
15 Detector shifting mechanism
17 Collimator control element
19 Image generation element
21 Reconstruction element
23 Imaging system detection element (Imaging system detection means)
25 Candidate point registration element (Candidate point registration means)
27 Start location determination element (Start location determination means)
31 Memory element
33 Input element
33a Candidate point registration switch (Registration directive means)
33b Start location determination switch (Determination directive means)
33c Imaging preparation switch
33d Imaging start switch
35 Main control element

What is claimed is:

1. An X-ray imaging apparatus, comprising:
an X-ray tube that irradiates an X-ray toward a subject;
an X-ray detector that detects the X-ray that transmits said subject and outputs an X-ray detection signal;
an imaging system shifting means that shifts an imaging system consisting of said X-ray tube and said X-ray detector in a body-axis direction of said subject;
an image generation element that generates a plurality of X-ray images using the X-ray detection signal that said X-ray detector outputs each time said imaging system shifting means shifts of said imaging system;
a reconstruction element that reconstructs a single long-length image by connecting said plurality of the X-ray images, which said image generation element generates, in the body-axis direction of said subject;
an imaging system detection means that detects as needed a present location of said imaging system that consists of said X-ray tube and said X-ray detector;
a candidate point registration means that registers a predetermined location comprising both ends of said long-length region as a candidate point;
a start location determination means that determines said candidate point that is closer to said present location of said imaging system as an imaging start location that is a location of said imaging system when taking a first X-ray image, and said candidate point that is farther from said present location of said imaging system as an imaging end location that is the location of said imaging system when taking a last X-ray image; and
a determination directive means that directs a determination of said imaging start location and said imaging end location that the start location determination means determines.

2. The X-ray imaging apparatus, according to claim 1, wherein:
said imaging system shifting means shifts said imaging system to said candidate point that said start location determination means determines to be said imaging start location.

3. The X-ray imaging apparatus, according to claim 1, further comprising:
a registration directive means that directs said candidate point registration means to register the present position of said imaging system as said candidate point.

4. The X-ray imaging apparatus, according to claim 2, further comprising:

a registration directive means that directs said candidate point registration means to register the present position of said imaging system as said candidate point.

* * * * *